US006388125B1

(12) United States Patent
Schmitz et al.

(10) Patent No.: US 6,388,125 B1
(45) Date of Patent: May 14, 2002

(54) PROCESS FOR PREPARING PHOSPHINIC ACIDS

(75) Inventors: Hans-Peter Schmitz, Brühl; Martin Sicken, Köln, both of (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/469,104

(22) Filed: Dec. 21, 1999

(30) Foreign Application Priority Data

Dec. 31, 1998 (DE) .......................................... 198 60 949
Nov. 16, 1999 (DE) .......................................... 199 55 741

(51) Int. Cl.$^7$ ................................................. C07F 9/30
(52) U.S. Cl. ......................................................... 562/8
(58) Field of Search ............................... 562/8; 423/316, 423/317

(56) References Cited

U.S. PATENT DOCUMENTS 4,366,150 A * 12/1982 Yamada et al.
4,582,691 A * 4/1986 Fujimoto et al. ........... 423/139
5,368,832 A * 11/1994 Buckholtz et al. .......... 423/316
6,184,405 B1 2/2001 Kleiner et al.

FOREIGN PATENT DOCUMENTS

| DE | 10 44 813 | 4/1957 |
| DE | 4 215 974 | 12/1992 |
| GB | 1 196 319 | 6/1970 |
| WO | WO 98/20012 | 5/1998 |

OTHER PUBLICATIONS

CA:119:117525 abs of PL 155955, Jan. 1992.*
CA:72:3569 abs of FR1545002, Nov. 1968.*
CA:102:38489 abs of Kompleksn. Ispol'z. Miner. Syr'ya by Anan'eva et al (7) pp. 28–31, 1984.*
CA:109:231292 abs of JP63057594, Mar. 1988.*
English Abstract of DE 1044813, Apr. 26, 1957.
Gmelins Handbuch der Anorganischen Chemie [Gmelins Handbook of Inorganic Chemistry], 8$^{th}$ Edition, vol. 16, Part C, pp. 94–96, Jan. 1, 1965.

* cited by examiner

*Primary Examiner*—Jean F. Vollano
(74) *Attorney, Agent, or Firm*—Anthony A. Bisulca

(57) ABSTRACT

The present invention relates to a process for the preparation of phosphinic acids from alkali metal phosphinates, which comprises reacting alkali metal phosphinates in a polar solvent with an inorganic mineral acid and then separating off the phosphinic acid formed.

4 Claims, No Drawings

PROCESS FOR PREPARING PHOSPHINIC ACIDS

FIELD OF THE INVENTION

The present invention relates to a process for the preparation of phosphinic acids from alkali metal phosphinates and to the use of the phosphinic acids prepared by this process.

DESCRIPTION OF THE RELATED ART

The term "phosphinic acids" means both phosphinic acid itself ("hypophosphorous acid", $H_3PO_2$, formula 1) and its organically substituted derivatives. Phosphinic acid is a product produced on a large scale which is used, for example, in large amounts as a reducing agent for electroless nickel-plating.

The organically substituted derivatives of phosphinic acid, such as methylphosphinic acid, also called "methylphosphonous acid" ($CH_3PO_2H_2$; formula 2, R=methyl), and the dialkylphosphinic acids ($R_2PO_2H$; formula 3), have acquired extensive industrial importance as intermediates, for example for the preparation of herbicides and flame retardants, and as extractants.

The various phosphinic acids are summarized by the formulae 1 to 3 given below.

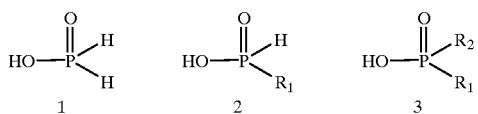

Numerous processes are described for the preparation of phosphinic acids (Gmelins Handbuch der Anorganischen Chemie [Gmelins Handbook of Inorganic Chemistry], 8th edition, Vol. 16, Part C, pp. 94–96).

For example, phosphinic acid can be prepared by cation exchange on an acidic ion exchanger resin from sodium phosphinate (R. Klement, Z. anorg. Ch. 260 [1949] 267/72).

Disadvantages are the requisite high amounts of ion exchanger resin with correspondingly low space/time yields, and the need for a complex waste-water treatment for the removal of phosphorus.

In addition, the reaction of sodium hypophosphite with sulfuric acid is described, where, however, the removal of sulfate requires the use of barium ions, which results in costly and complex work-up with the disposal of barium sulfate slurries.

U.S. Pat. No. 5,578,182 describes a process for the preparation of phosphinic acid which is based on the electrochemical conversion of sodium phosphinate to phosphinic acid by means of complex electrodialysis.

DE-A-4215974 describes a method of reacting sodium phosphinate with aqueous hydrochloric acid, then precipitating out sodium chloride by concentration and thus obtaining an aqueous phosphinic acid after filtration. A disadvantage of this process is, inter alia, the residual content of sodium chloride in the phosphinic acid. The patent therefore proposes the removal of the residual chloride ions by a downstream ion exchange, but this means significantly higher expenditure and does not solve the sodium ion problem since these ions still remain in the product.

All of the processes described above either involve complicated technical measures or produce considerable amounts of unuseful waste salts as byproducts. Moreover, these processes cannot be used for the preparation of the industrially very interesting, organically substituted phosphinic acids.

BRIEF SUMMARY OF THE INVENTION

The object of the present invention is thus to provide a process for the preparation even of organically substituted phosphinic acids which can be carried out in a simple manner and which produces high-purity products. All products which form during the process should be reusable, and consequently the process can be carried out in a particularly economical and environmentally friendly manner.

This object is achieved by a process of the type mentioned in the introduction, which comprises reacting alkali metal phosphinates in a polar solvent with an inorganic mineral acid and then separating off the phosphinic acid formed.

DETAILED DESCRIPTION OF THE INVENTION

Preferably, the polar solvent used is acetic acid, propionic acid and/or an alcohol. Suitable examples are ethanol, propanol, butanol and other short-chain alcohols.

Particularly preferably, the alkali metal phosphinates are sodium phosphinates of the formulae 4, 5 and/or 6,

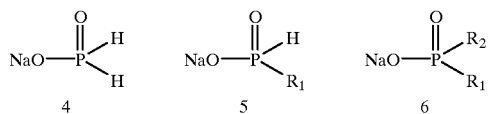

in which $R_1$ and $R_2$ are identical or different and are a $C_1$ to $C_{20}$-alkyl group (linear, branched or cyclic), $C_1$ to $C_{20}$-aryl group or $C_1$ to $C_{20}$-alkylaryl group.

Preferably, the inorganic mineral acid is hydrochloric acid, sulfuric acid or phosphoric acid or mixtures thereof.

Particularly preferably, the alkali metal phosphinates are phosphinic acid sodium salt, methylphosphinic acid sodium salt, methylethylphosphinic acid sodium salt and/or diethylphosphinic acid sodium salt.

Preference is given to reacting alkali metal phosphinate and inorganic mineral acid together in equivalent amounts.

The invention also relates to the use of the phosphinic acids obtained by the process described above for the preparation of flame retardants, crop-protection compositions and extractants.

Using the process according to the invention, it has now been found, surprisingly, that virtually salt-free, pure phosphinic acids can be obtained in a simple manner from alkali metal phosphinates by precipitating out the alkali metal ions present therein with inorganic mineral acids in polar, preferably acidic organic solvents. This novel process is based on the fact that alkali metal phosphinates and their corresponding phosphinic acids are extremely soluble in the abovementioned solvents, whereas the mineral salts of the alkali metals are virtually insoluble.

The phosphinic acids can therefore be prepared in a simple manner by adding a corresponding equivalent amount of inorganic mineral acid to the particular acidic solution of the alkali metal phosphinate and filtering off the alkali metal salt which has then precipitated out completely. If readily volatile mineral acids are used, these can also be employed in excess.

The resulting phosphinic acid solution can either be processed without further work-up or be converted into the pure, salt-free phosphinic acid by distillative removal and recovery of the solvent used. Further purification is not usually necessary, but can, for example, be carried out by distillation.

The alkali metal salts precipitated out by the process according to the invention are produced in high purity and can, after washing and drying, be reused, for example, as raw material in chlor-alkali electrolysis (NaCl) or as a filler ($Na_2SO_4$).

The process according to the invention thus offers considerable economic and commercial advantages, since high-purity phosphinic acids can be produced at low expenditure and using simple process technology, and also advantages which are relevant from an environmental point of view, since only reusable substances of value are formed. A further advantage is that the process according to the invention can be used for a large number of inorganically and organically substituted phosphinic acids.

In the process according to the invention, anhydrous feed substances are advantageously used, since the immediate complete alkali salt precipitation is possible only at low water contents. It is, however, also possible to use hydrous alkali metal phosphinates or phosphinic acids, since it is possible to remove the water from the abovementioned solvent used by distillation before or after the alkali metal salt precipitation without any problem.

The invention is illustrated by the examples below.

EXAMPLE 1

In a 1 l three-neck flask fitted with stirrer and dropping funnel, 49 g of 98% strength sulfuric acid (0.5 mol) are added to a solution of 88 g of sodium phosphinate (1 mol) in 500 ml of acetic acid at room temperature and with stirring over the course of 30 min. The salt which precipitates out is filtered off and washed with 2×100 ml of acetic acid. Drying for 2 h at about 50° C. in a water-pump vacuum gives 71 g (yield>99%) of sodium sulfate (residual moisture<0.5%, purity>99%).

The combined filtrates comprise 66 g of pure phosphinic acid ($^{31}$P-NMR analysis: 14.6 ppm, purity: >99%, mol % of P). The solvent acetic acid can be removed at 40° C. under reduced pressure (1 torr).

EXAMPLE 2

In a 1 l three-neck flask fitted with stirrer and dropping funnel, 49 g of 98% strength sulfuric acid (0.5 mol) are added to a solution of 102 g of methylphosphinic acid sodium salt (1 mol) in 500 ml of acetic acid at room temperature and with stirring over the course of 30 min. The salt which precipitates out is filtered off and washed with 2×100 ml of acetic acid. Drying for 2 h at about 50° C. in a water-pump vacuum gives 71 g (yield>99%) of sodium sulfate (residual moisture<0.5%, purity>99%). The combined filtrates comprise pure methylphosphinic acid. The acetic acid is distilled off at about 80° C. in a water-pump vacuum, giving 80 g of methylphosphinic acid in the form of a clear, colorless liquid ($^{31}$P-NMR analysis: 33.4 ppm, purity: >99%, mol % of P; $bp_1$: 105° C.).

EXAMPLE 3

In a 1 l three-neck flask fitted with stirrer and dropping funnel, 49 g of 98% strength sulfuric acid (0.5 mol) are added to a solution of 144 g of diethylphosphinic acid sodium salt (1 mol) in 500 ml of acetic acid at room temperature and with stirring over the course of a period of 30 min. The salt which precipitates out is filtered off and washed with 2×100 ml of acetic acid. Drying for 2 h at about 50° C. in a water-pump vacuum gives 71 g (yield>99%) of sodium sulfate (residual moisture<0.5%, purity>99%). The combined filtrates comprise pure diethylphosphinic acid. The acetic acid is distilled off at about 100° C. in a water-pump vacuum, giving 122 g of diethylphosphinic acid (yield>99%) in the form of a clear, colorless liquid. ($^{31}$P-NMR analysis: 57.4 ppm, purity: >99%, mol % of P; $bp_{0.4}$: 126° C.).

EXAMPLE 4

In a 1 l three-neck flask fitted with stirrer and dropping funnel, 100 g of 36% strength hydrochloric acid (1 mol) are added to a solution of 144 g of diethylphosphinic acid sodium salt (1 mol) in 500 ml of acetic acid at room temperature and with stirring over the course of 30 min. The water which has been introduced is then driven off via a distillation column. The salt which precipitates out is filtered off and washed with 2×100 ml of acetic acid. Drying for 2 h at about 50° C. in a water-pump vacuum gives 58 g (yield>99%) of sodium chloride (residual moisture<0.5%, purity>99%). The combined filtrates comprise pure diethylphosphinic acid. The acetic acid is distilled off at about 100° C. in a water-pump vacuum, giving 122 g of diethylphosphinic acid (yield>99%) in the form of a clear, colorless liquid ($^{31}$P-NMR analysis: 57.4 ppm, purity: >99%, mol % of P; $bp_{0.4}$: 126° C.).

EXAMPLE 5

In a 1 l three-neck flask fitted with stirrer and dropping funnel, 49 g of 98% strength sulfuric acid (0.5 mol) are added to a solution of 106 g of sodium phosphinate monohydrate (1 mol) in 500 ml of acetic acid at room temperature and with stirring over the course of 30 min. The water which has been introduced is then driven off via a distillation column. The salt which precipitates out is filtered off and washed with 2×100 ml of acetic acid. Drying for 2 h at about 50° C. in a water-pump vacuum gives 71 g (yield>99%) of sodium sulfate (residual moisture<0.5%, purity>99%). The combined filtrates comprise 66 g of pure phosphinic acid. ($^{31}$P-NMR analysis: 14.6 ppm, purity: >99%, mol % of P). The solvent acetic acid can be removed at 40° C. under reduced pressure (1 torr).

EXAMPLE 6

In a 1 l three-neck flask fitted with stirrer and dropping funnel, 100 g of 36% strength hydrochloric acid (1 mol) are added to a solution of 102 g of methylphosphinic acid sodium salt (1 mol) in 400 ml of butanol at room temperature and with stirring over the course of 30 min. The water which has been introduced is then driven off via a water separator. The sodium chloride which precipitates out is filtered off and washed with 2×100 ml of butanol. Drying for 1 h at about 50° C. in a water-pump vacuum gives 58 g (yield>99%) of sodium chloride (residual moisture<0.1%, purity>99%). The combined filtrates comprise pure methylphosphinic acid. The butanol is distilled off at about 50° C. in a water-pump vacuum, giving 80 g of methylphosphinic acid in the form of a clear, colorless liquid ($^{31}$P-NMR analysis: 33.4 ppm, purity>99%, mol % of P; $bp_1$: 105° C.).

What is claimed is:
1. A process for the preparation of phosphinic acids from alkali metal phosphinates, which comprises the steps of; reacting alkali metal phosphinates, corresponding to the formula 4, 5 and 6

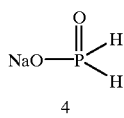 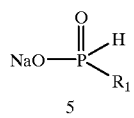 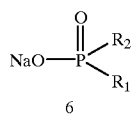

4    5    6 in which $R_1$ and $R_2$ are identical or different and are a $C_1$ to $C_{20}$-alkyl group (linear, branched or alkyl), $C_1$ to $C_{20}$-aryl group or $C_1$ to $C_{20}$-alkylaryl group, in a polar solvent with an inorganic mineral acid; separating off the phosphinic acid formed; and filtering off an alkali metal salt, said polar solvent selected from acetic acid, propionic acid or an alcohol, said inorganic mineral acid selected from hydrochloric acid, sulfuric acid, phosphoric acid and mixtures thereof.

2. The process as claimed in claim 1, wherein $R_1$ and $R_2$ are identical or different and are a $C_1$ to $C_6$-alkyl group (linear, branched or cyclic).

3. The process as claimed in claim 1, wherein the alkali metal phosphinate is sodium phosphinate, methylphosphinic acid sodium salt, methylethylphosphinic acid sodium salt and/or diethylphosphinic acid sodium salt.

4. The process as claimed in claim 1, wherein alkali metal phosphinate and inorganic mineral acid are reacted together in equivalent amounts.

* * * * *